United States Patent
Hu et al.

(10) Patent No.: US 7,474,971 B2
(45) Date of Patent: Jan. 6, 2009

(54) METHOD AND APPARATUS FOR CHARACTERISING MULTIPHASE FLUID MIXTURES

(75) Inventors: Shenggen Hu, Westlake (AU); Bruce Firth, Bellbowrie (AU)

(73) Assignee: Commonwealth Scientific and Industrial Research Organization, Campbell (AU)

( * ) Notice: Subject to any disclaimer, the term of this patent is extended or adjusted under 35 U.S.C. 154(b) by 0 days.

(21) Appl. No.: 10/546,783

(22) PCT Filed: Feb. 17, 2004

(86) PCT No.: PCT/AU2004/000187

§ 371 (c)(1),
(2), (4) Date: Oct. 12, 2005

(87) PCT Pub. No.: WO2004/077036

PCT Pub. Date: Sep. 10, 2004

(65) Prior Publication Data

US 2006/0265150 A1    Nov. 23, 2006

(30) Foreign Application Priority Data

Feb. 26, 2003 (AU) ................ 2003900857

(51) Int. Cl.
*G06F 19/00* (2006.01)

(52) U.S. Cl. ............... 702/65; 702/50; 73/861.22; 73/861.24; 73/861.355; 73/861.357

(58) Field of Classification Search ............ 702/251, 702/48, 65, 50; 73/61.45, 64.44, 861.02, 73/861.04, 861.06, 861.35, 861.44, 861.45, 73/861.63, 861.22, 861.24, 861.355, 861.357

See application file for complete search history.

(56) References Cited

U.S. PATENT DOCUMENTS

| | | | |
|---|---|---|---|
| 3,523,245 A | | 8/1970 | Love et al. |
| 4,266,425 A | | 5/1981 | Allport ........................ 73/61 |
| 5,033,288 A | * | 7/1991 | Castel ..................... 73/61.44 |
| 5,224,372 A | * | 7/1993 | Kolpak .................... 73/19.03 |
| 5,259,250 A | * | 11/1993 | Kolpak ................. 73/861.355 |
| 5,608,170 A | * | 3/1997 | Atkinson et al. ......... 73/861.04 |
| 5,661,237 A | * | 8/1997 | Dussan V. et al. ........ 73/152.18 |
| 5,714,691 A | * | 2/1998 | Hill .......................... 73/861.04 |
| 5,837,902 A | * | 11/1998 | Veneruso et al. ......... 73/861.06 |
| 5,948,995 A | * | 9/1999 | Veneruso et al. ......... 73/861.06 |

(Continued)

FOREIGN PATENT DOCUMENTS

JP          08271469 A    *  10/1996

(Continued)

OTHER PUBLICATIONS

International Search Report for PCT/AU2004/000187 dated Apr. 20, 2004.
Thorn et al., *Recent development in three-phase flow measurement*, Meas. Sci. Technol. 8 (1997) 691-701.
Beck et al., *Process tomography: a European innovation and its applications*, Meas. Sci. Technol., No. 7 (1996), pp. 215-224.

(Continued)

*Primary Examiner*—Carol S Tsai
(74) *Attorney, Agent, or Firm*—Nixon & Vanderhye, PC

(57) ABSTRACT

An example method for determining at least one characteristic of a multiphase fluid includes applying alternating energy of predetermined amplitude to a portion of a multiphase fluid and measuring the electrical impedance spectrum across the portion of the multiphase fluid, whereby a characteristic of the multiphase fluid can be determined from the measured electrical impedance spectra.

6 Claims, 9 Drawing Sheets

U.S. PATENT DOCUMENTS

| | | | | |
|---|---|---|---|---|
| 6,097,786 | A  * | 8/2000 | Groves et al. | 378/53 |
| 6,334,957 | B1 * | 1/2002 | Waskaas | 210/739 |
| 6,405,604 | B1 * | 6/2002 | Berard et al. | 73/861.63 |
| 6,467,358 | B1 * | 10/2002 | Nishi et al. | 73/861.04 |
| 6,655,221 | B1 * | 12/2003 | Aspelund et al. | 73/861.04 |
| 6,782,736 | B1 * | 8/2004 | Hammer | 73/61.44 |
| 6,912,918 | B1 * | 7/2005 | Lynnworth et al. | 73/861.26 |
| 7,096,719 | B2 * | 8/2006 | Gysling | 73/61.75 |
| 2003/0010126 | A1 * | 1/2003 | Romanet et al. | 73/649 |
| 2003/0011386 | A1 * | 1/2003 | Xie et al. | 324/694 |
| 2004/0012395 | A1 * | 1/2004 | Salamitou | 324/444 |

FOREIGN PATENT DOCUMENTS

WO        03/014729        2/2003

OTHER PUBLICATIONS

Ceccio et al., *A Review of Electrical Impedance Techniques for the Measurement of Multiphase Flows*, Journal of Fluids Engineering, vol. 118, Jun. 1996, pp. 391-399.

Darowicki, Kazimierz; "The Amplitude Analysis of Impedance Spectra"; Electrochimica Acta.; vol. 40; pp. 439-445; 1995.

M.S. Beck et al.; "Process Tomography: A European Innovation and its Applications"; Meas. Sci. Technol. 7. pp. 215-224; 1996.

F,C, Fonseca et al.; "Grain-Sized Influence on the Phase Transition of $Bi_{26}Mo_9WO_{69}$: AN-X-Ray Diffraction and Impedance Spectroscopy Study"; Solid State Ionics, vol. 140; pp. 161-171; 2001.

EPO Communication dated Dec. 19, 2007, in Application 04711539.9-2204.

* cited by examiner

METHOD AND APPARATUS FOR CHARACTERISING MULTIPHASE FLUID MIXTURES

This application is the U.S. national phase of international application PCT/AU2004/000187 filed 17 Feb. 2004 which designated the U.S. and claims benefit of AU 2003900857 filed 26 Feb. 2003, the entire contents of each of which are hereby incorporated by reference.

TECHNICAL FIELD

This invention relates to a method and apparatus for characterising multiphase fluid mixtures (e.g. slurries, emulsions, suspension of bubbles and fine solids in liquid, and bubble froth phase) based on the analysis of electrical impedance spectrum using predictive mathematical algorithms, such as artificial neuron network.

BACKGROUND OF THE INVENTION

In many industrial processes involving multiphase fluid mixtures where the components and mixtures may be stationary, moving in bathes or flowing continuously, there are needs for accurate and inexpensive phase concentration monitoring methods and means. It is also often desirable that these methods and means have the capability of working on-line with the processes.

A number of methods have been used in the past to monitor the phase concentration of multiphase fluid mixtures. Generally these methods seek to find a specific property which is significantly different for the phases. The value of this property for the mixture will then depend on the phase concentration. By measuring this property one would be able to find the phase concentration. Examples of the specific property are electrical properties (i.e. conductivity or capacitance), density, viscosity, absorption of light or absorption of radioactive radiation.

Precise and safe measurement of conductivity or capacitance requires relatively simple instrumentation. Thus, methods based on conductivity or capacitance have been widely used in practice for measuring phase concentrations not only in solids-liquid systems but also in gas-liquid, liquid-liquid and three-phase systems.

Examples of conductivity or capacitance based devices are disclosed in U.S. Pat. No. 4,266,425 to Allport et al., U.S. Pat. No. 3,523,245 to Love et al.

The prior art systems described above, however, have a few of major drawbacks. Electrical conductivity based methods are very sensitive to the variations in the electrical conductivity of the liquid phase of the multiphase fluid mixture. For example, the electrical conductivity of an aqueous slurry may increase by more than 50 times with the addition of 2.5% by weight of salt (NaCl) to the aqueous phase. When the conductivity of the liquid phase changes substantially with time, the conductivities of both the slurry mixture and the liquid phase are required in order to calculate the solids concentration. But the on-line measurement of the conductivity of the liquid phase in a slurry mixture is generally difficult due to the requirement of phase separation. Electrical conductivity based methods are also generally difficult to apply to multiphase fluid mixtures having very low electrical conductivity. The capacitance based methods can be applied only to multiphase fluid mixture where the continuous phase is nonconductive. In the case with aqueous slurries, the high electrical conductivity of the aqueous phase interferes with the dielectric measurement.

In determining the water content of oil/water emulsion mixtures, prior art systems have a significant limitation because of the fact that the electrical properties of water-continuous and oil-continuous emulsions are quite different even if the water content is identical. Prior art systems have also failed to provide methods or means for determining phase composition in fluid mixtures with more than two phases. This is because that different sets of phase compositions may result in similar conductivity or capacitance measurements. Most of prior art systems failed to give accurate measurements when the concentration of the disperse phase in a two phase fluid mixture is low.

The limitation of conductivity or capacitance based methods is attributed to the limited information obtained at a single frequency of excitation alternating current (AC) signal. One known value of mixture conductivity or capacitance is insufficient to determine the phase composition when both the phase composition and the electrical properties of one of the phases in the mixture are unknown.

In certain industrial processes, such as dense medium separation of coal and mineral ores and grinding circuits in mineral processing industry, it is desirable to monitor the average particle size of suspended fine particles in an aqueous slurry under the condition of high solids concentration. At present there are no simple commercially available on-line particle size monitors capable of this measurement. The conventional method of measuring particle size distribution is to remove samples from the streams of interest and to perform screen analyses on these samples. However, screen analysis can provide a reasonably accurate determination of particle size distribution above about 45 microns. There are three commercially available on-line particle size analysers based on ultrasonic attenuation, a scanning laser microscope and a reciprocating caliper. However, these analysers are not suitable for use in slurry mixtures where the average particle size is below 45 micron or the solids concentration is high or the fluid medium is not transparent.

Froth flotation is widely used for concentrating minerals, or other valuable constituents, from their ores or other raw materials. Minerals are separated from gangue particles by taking advantage of their differences in hydrophobicity. These differences can occur naturally, or can be controlled by the addition of a collector reagent. Froth flotation generally involves the use of air injection through a slurry that contains water, minerals and gangue particles within a vessel. Dispersed air bubbles attract the hydrophobic valuable minerals and carry them upward to the top of the flotation cell, whereupon they form a froth bed or froth layer which contains and supports pulverised mineral. The froth is then scraped or permitted to flow over the lip of the cell to effect the separation. The thus concentrated mineral bearing froth is collected and further processed to improve the concentration of desired minerals. The pulp may be further processed to recover other valuable minerals.

On-line measurement of process parameters is a prerequisite for froth flotation process control. Whereas some process parameters can be monitored on-line with cost effective and reliable measuring devices, the effective on-line monitoring and optimal control of froth flotation processes are still far from being achieved because of the strong inertia of the flotation process, a still inadequate knowledge of suitable variables for the on-line monitoring of the process efficiency and the lack of appropriate on-line measurement instrumentation.

The froth phase in a froth flotation process has a number of characteristics, including bubble size, stability, mobility, solids content and water content. The effects of operating conditions such as reagent type, reagent dosage, water chemistry, pulp level, feed flowrate and aeration rate are reflected in the froth characteristics.

The characteristics of froth layer are related to flotation grade and recovery. In view of the difficulty in the direct measurement of the froth characteristics, it is desirable to use other froth properties that can be easily on-line measured as monitoring tools and are closely related to flotation grade and recovery.

SUMMARY OF THE INVENTION

The present invention provides an alternative method and apparatus for characterising multiphase fluid mixtures preferably where the components and mixtures may be stationary, moving in bathes or flowing continuously in a conduit, and more particularly a method and apparatus for determining the proportion of each phase constituting a multiphase fluid mixture, the type of oil/water emulsion mixtures, the particle size of fine particles in liquid-solids slurries and the characteristics of bubble froth phase.

In the description hereafter, "electrical impedance spectrum" refers to the complex plane plot of imaginary verses real impedance values for a plurality of different frequencies of energy or in the plotting of quantities derived from the real and imaginary impedance values.

According to one aspect of the present invention there is provided a method for determining at least one characteristic of a multiphase fluid including the steps of applying alternating energy of a predetermined amplitude to a portion of a multiphase fluid and measuring the electrical impedance spectrum across the portion of multiphase fluid whereby a characteristic of the multiphase fluid can be determined from the measured electrical impedance spectra.

It is preferred that the above method is repeated for a plurality of different amplitudes of alternating energy.

It is preferred that the alternating energy includes alternating voltage and alternating current.

Preferably the electrical impedance spectrum is measured across the portion of multiphase fluid for an AC voltage of constant amplitude or AC current of constant amplitude.

Preferably the alternating energy is applied across electrodes in the portion of multiphase fluid.

The term "electrodes" should be interpreted in its broadest sense to include any terminal, wires, or similar points across which current or voltage can be applied to measure the electrical impedance spectrum.

It is preferred that the electrodes are set a predetermined distance apart and electrical impedance measurements are made at the predetermined distance of separation between electrodes.

According to one preferred embodiment of the invention there is provided an apparatus for characterising multiphase fluid mixtures, the apparatus including:

an electrode pair comprising at least one conductive path and defining therebetween and thereabout a sample zone within the multiphase fluid mixture, a measuring means for measuring characteristics of the electrical field formed between the electrode pair, and computing means for collecting information from the measuring means and converting it to a desired form of output.

According to one embodiment of the invention the apparatus includes two electrodes.

Preferably the EIS is measured across the electrodes for a constant amplitude of potential difference (voltage).

According to another embodiment the apparatus includes three electrodes.

Preferably the current between adjacent electrodes is set at a predetermined amplitude.

It is preferred that the voltage is measured across the three electrodes.

According to a further embodiment of the present invention the apparatus includes four electrodes.

Preferably the four electrodes comprise two pairs of electrodes each adapted to provide a constant magnitude of current between the pairs of electrodes.

Preferably the measuring means is adapted to measure the change in voltage between the pairs of electrodes.

It is preferred that the apparatus includes a configuration of electrodes in which either a current of constant amplitude is applied across the electrodes, a voltage of constant amplitude is applied across the electrodes or a combination of current of constant amplitude and voltage of constant amplitude is applied across respective adjacent electrodes.

It is preferred that a current of constant amplitude is provided by grouping a pair of electrodes.

According to another embodiment it is preferred that electrical impedance spectra are measured for different values of constant voltage or alternatively different values of constant current.

According to one aspect of the present invention there is provided a method for characterising a multiphase fluid mixture, the method including the steps of applying an alternating current or voltage to the electrodes located in the multiphase fluid mixture, measuring the electrical impedance spectrum across the electrodes at one or a few selected amplitudes of excitation signal;

transforming the measured electrical impedance spectrum or spectra into a few indicator quantities using feature extraction algorithms; and determining, from the indicator quantities of the measured electrical impedance spectrum, at least one characteristic of at least one phase constituent in the mixture using a predictive mathematical model.

According to one embodiment, the invention involves measuring the real and imaginary parts of the impedance over a frequency range of 0.1 Hz to 1 MHz. Real and imaginary impedance values preferably include real and imaginary components of mathematically related parameters such as impedance, admittance, modulus and dielectric permittivity, etc. The impedance sensing means may be configured in two or three or four electrodes.

It is preferred that the method includes the step of measuring temperature and pH value of the multiphase fluid mixture at each measurement frequency or measured impedance spectra.

The multiphase fluid mixtures preferably include matter such as gas, solid, liquid or different combinations of the above.

It is preferred that the method includes the step of transforming the measured electrical impedance spectrum into a few indicator quantities. The step of transforming further includes obtaining data in the form of average number of good readings, calculating a smoothed electrical impedance spectrum using 2D data smoothing algorithms, such as locally weighted regression, and scaling indicator quantities and temperature and pH readings into suitable value ranges. The indicator quantities of the electrical impedance spectrum may further include the real and imaginary impedance values at a number of selected frequencies, first and second derivatives of the spectrum at a number of selected frequencies, average values of imaginary impedance component over a selective range of real impedance, the parameters of a mathematical model for the representation of the impedance spectrum, and the latent variables, summarising the information contained in the original impedance spectrum, calculated from multivariate statistical methods, such as principal component analysis (PCA) and partial least-squares (PLS).

The method preferably includes calculating indicator quantities by fitting the electrical impedance spectrum to a mathematical model of the impedance spectrum. The mathematical model may further include an electrical equivalent circuit model and empirical regression equations.

Preferably the method includes the step of determining, from the indicator quantities combined with temperature and pH, at least one characteristic of at least one phase constituent in the mixture using a predictive mathematical model. The characteristics further include the proportion of each phase constituting a multiphase fluid mixture, the type of oil/water emulsion mixtures, the particle size of fine particles in liquid-solids slurries and the characteristics of bubble froth phase. The predictive mathematical model further include a trained artificial neural network and a multivariate regression model.

It is preferred that the method includes training and validating an artificial neural network with a number of indicator quantities with known characteristics of multiphase fluid mixtures. The method further includes calculating parameters in a predictive mathematical model using a number of indicator quantities with known characteristics of multiphase fluid mixtures.

It is preferred that the method includes the step of analysing the impedance spectrum using pattern matching algorithms to determine whether characteristics of a bubble froth phase loaded with particles are favorable or not in terms of the grade and yield of the flotation concentrate.

The method preferably includes the step of analysing the impedance spectrum using pattern matching algorithms to determine whether an oil/water emulsion is oil continuous or water continuous type.

According to a further aspect of the present invention there is provided a method of analysing extraneous matter in a fluid including the steps of receiving impedance data, being data including real and imaginary impedance values measured across electrodes located in a fluid, recording the impedance spectrum at a plurality of time intervals, calculating indicator quantities of the impedance spectrum for the received impedance spectrum data, comparing indicator quantities of the impedance spectrum with reference indicator quantities and determining at least one characteristic of at least one phase constituent in the mixture from the comparing steps.

The method may include the step of determining characteristics of multiphase fluid mixtures in the forms of numerical value or qualitative index.

It should be noted that reference to electrical impedance spectrum refers to EIS (Electrical Impedance Spectrum).

It is to be understood that, if any prior art publication is referred to herein, such reference does not constitute an admission that the publication forms a part of the common general knowledge in the art, in Australia or in any other country.

The words "comprising, having, including" should be interpreted in an inclusive sense, meaning that additional features may also be added.

BRIEF DESCRIPTION OF DRAWINGS

Preferred embodiments of the present invention will now be described by way of example only with reference to the accompanying drawings in which.

It should be understood that the embodiments of the invention described hereinafter with reference to the drawings refer to specific electrode configurations where the electrode type, number of electrodes and distance between electrodes remains fixed. The invention also covers other embodiments where different numbers and distances between electrodes are provided as well as different types of electrodes. In these other embodiments values of electrical impedance would be different to those exemplified in the preferred embodiments.

DETAILED DESCRIPTION

According to one embodiment of the present invention the electrical impedance spectrum of a multiphase fluid mixture was measured over a wide range of frequencies to identify characteristic parameters of interest in a multiphase fluid mixture. In addition the inventors noted the dependence of electrical properties of constituents in multiphase fluid mixtures upon excitation by an AC signal varies. It was therefore considered that the electrical impedance spectrum of a multiphase fluid mixture measured over a wide range of frequency may contain sufficient information for deducing characteristic parameters of interest.

The inventors also realised that electrical and dielectric properties of solids-liquid suspensions depend on not only the phase composition but also the particle size of solids. When an AC current is passing through a suspension, the surface charge and the associated electrical double layer of particles tend to cause a phase shift of the AC current in a certain range of frequency due to charge relaxation processes on the surface. For a given volume fraction of suspended particles, the smaller the particle size, the higher the amount of the surface charge. Since the phase shift is proportional to the amount of the surface charge, small particles will cause a higher phase shift than large particles. It is, therefore, possible to calculate the particle size from measured real and imaginary parts of electrical impedance over a wide range of frequency.

Furthermore the inventors discovered that the electrical and dielectric properties of components in a froth phase are different from each other.

From the viewpoint of electrical behaviour of the froth phase, the inter-bubble lamellae containing water and solids can be regarded as a complex network of electrical conductance, inductance and capacitance. The structure of this network would be sensitive to changes in the froth structure and characteristics. Therefore, the measurement of the electrical impedance of the froth phase over a wide range of frequencies would probe into the froth structure and/or characteristics.

Figure 1:
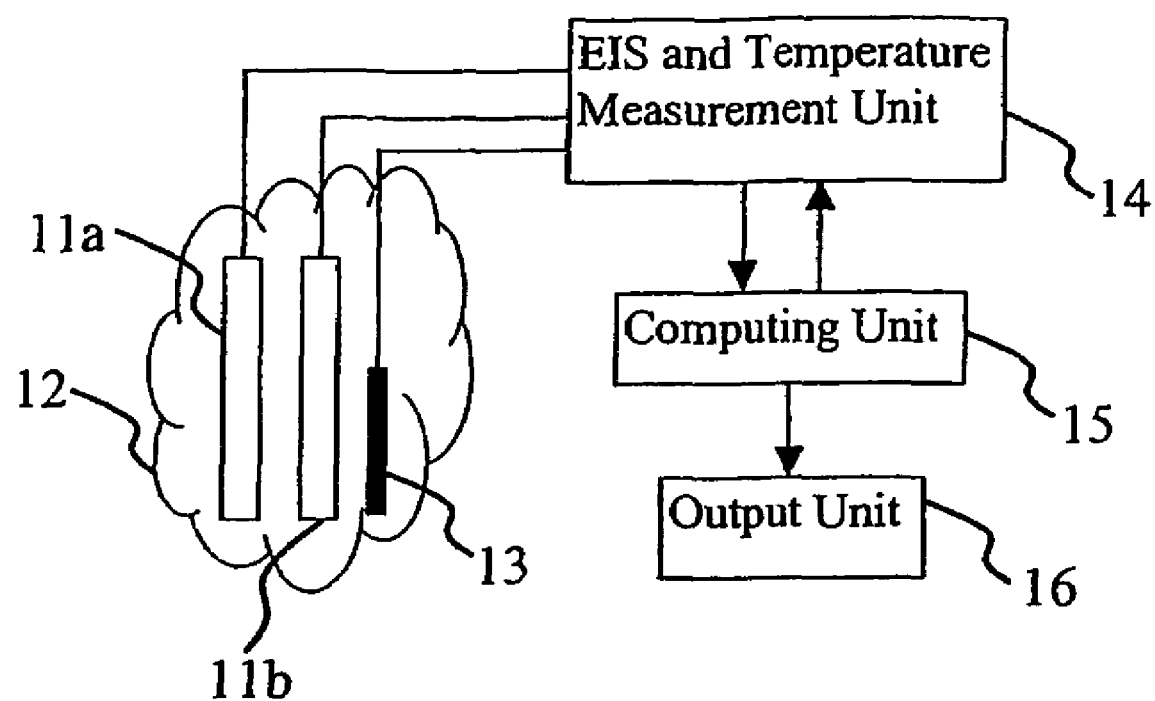
FIG. 1 is a block diagram of the measurement apparatus for characterising multiphase fluid mixtures according to a first embodiment of the present invention.
Figure 2A:
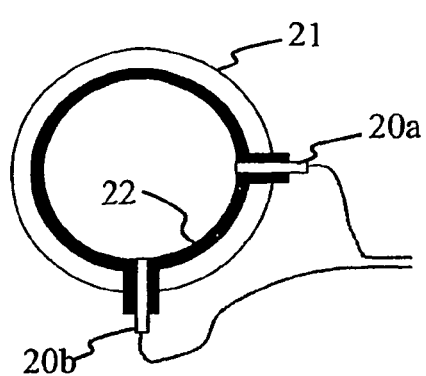
FIGS. 2A, 2B, 2C and 2D are schematic diagrams illustrating possible designs of electrode pairs useful for the measurement of electrical impedance spectrum.
Figure 2B:
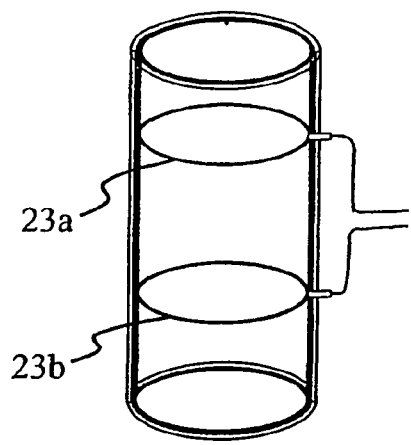
Figure 2C:
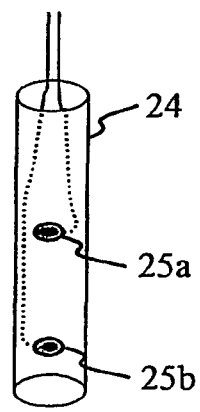
Figure 2D:
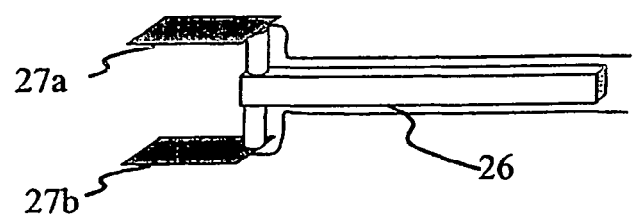

As shown in FIG. 1 an apparatus for characterising multiphase fluid mixtures consists of a pair of fluid measurement electrodes 11a and 11b immersed in multiphase fluid mixtures 12, a temperature sensor 13, an EIS and temperature measurement unit 14, a computing unit 15 and an output unit 16.

Referring to FIGS. 2A-2D, the measurement electrodes can be mounted on the inner surface of a conduit or vessel wall in the forms of tapped rods 20a and 20b or rings 23a and 23b. Alternatively the electrodes can be mounted on a non-conductive rod 24 in the form of dots 25a and 25b, or on a non-conductive spacer 26 in the form of plates 27a and 27b with any suitable shapes. Instead of the plate type of electrodes 27a and 27b, one electrode may be a rod electrode surrounded coaxially by another cylindrical electrode. In the cases with a conductive conduit or vessel wall, the electrodes 20a and 20b have to be insulated with the conductive wall 21 and a non-conductive layer 22 has to be applied to cover the inner surface of the conductive wall 21. The material for non-conductive layer 22 includes certain ceramics, casting basil, plastics and other suitable materials.

An electrical impedance spectrum and temperature measurement unit 14 is connected to each of electrodes as well as to the computing unit 15. The measurement unit 14 sends and receives signals to or from the computing unit 15 through electrical, optical, electromagnetic wireless or other type signals. The output unit 16 preferably is a visual displayer, e.g. LCD, for displaying the results provided by the computing unit 15.

The measurement unit 14 preferably includes a signal generation module for generating AC signals at specified amplitude and frequencies, a measuring module for measuring the amplitude and phase angle of AC signals, a temperature measurement circuit, self calibration and diagnosis circuits and an embedded microprocessor for controlling signal generation and measuring module and sending and receiving signals to or from the computing unit 15.

The computing unit 15 preferably includes means for outputting control variables or commands to the measurement unit 14, means for receiving and recording measured temperature, real and imaginary impedance values for a plurality of different frequencies, means for checking the validity of received data, means for scaling the received data into a suitable value range, means for calculating indicator quantities from the measured EIS, means for clustering the data into data patterns and means for determining at least one of characteristics of multiphase fluid mixtures from the indicator quantities.

By measuring the electrical impedance spectrum across the fluid measurement electrodes 11a and 11b, information about characteristics of multiphase fluid mixtures can be identified. The multiphase fluid mixtures preferably include matter such as gas, solid, liquid or different combinations of the above.

Figure 3A:
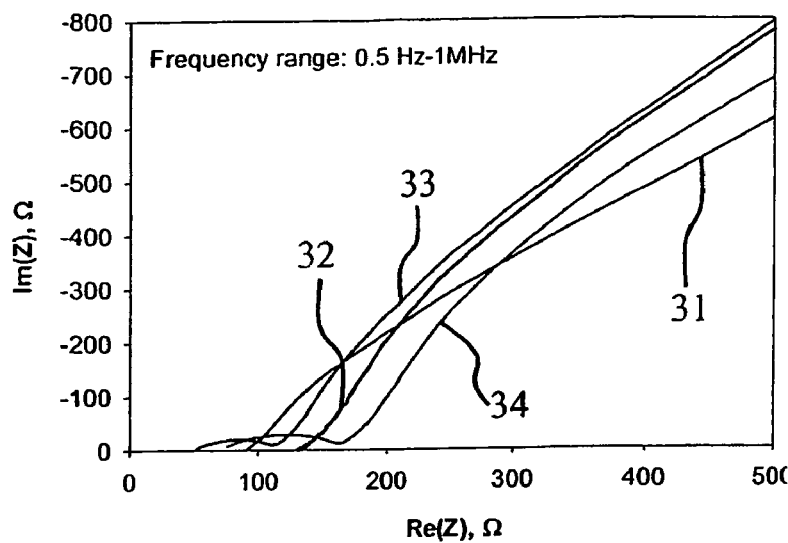
FIGS. 3A and 3B show graphical representations of electrical impedance spectra of liquid-solids slurries with different compositions.
Figure 3B:
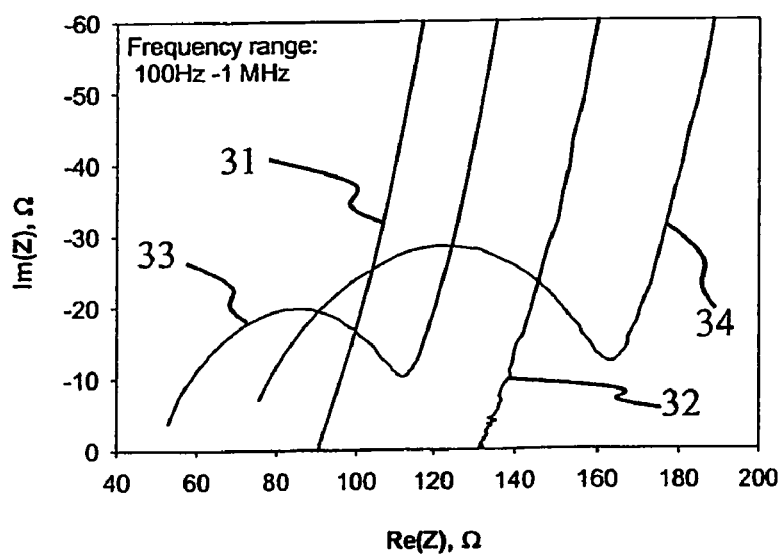

For example as shown in FIGS. 3A and 3B the effects of phase composition on electrical impedance spectrum of slurries can be ascertained. Electrical impedance spectra for water only, water slurry containing 20% (by volume) sands, water slurry containing 12% magnetite and water slurry containing 10% magnetite and 20% sands are represented by 31, 32, 33, 34, respectively. FIG. 3A shows the spectra for the frequency range of 0.5 Hz to 1 MHz. In order to emphasise the effects of phase composition on EIS, the same spectra only in the frequency range of 100 Hz to 1 MHz is shown in FIG. 3B. FIGS. 3A and 3B clearly indicate that the EIS is sensitive to the changes of phase composition of aqueous slurry mixtures. It is this sensitivity that provides the basis for the present invention. It can be also seen that the effect of the presence of magnetite on the spectrum is substantially different from that of sand. The presence of magnetite can cause a peak in the high frequency range of the spectrum, but sand cannot. The ability of the apparatus in the present invention to distinguish the relative composition of different dispersed phases is based on their different effects on the spectrum. The measurement of the spectra as shown in FIGS. 3A and 3B can be repeated at a few different amplitudes of the excitation signal and the determination of the amplitude dependence of the spectra would allow the further differentiation of factors causing the changes of the EIS.

Figure 4A:
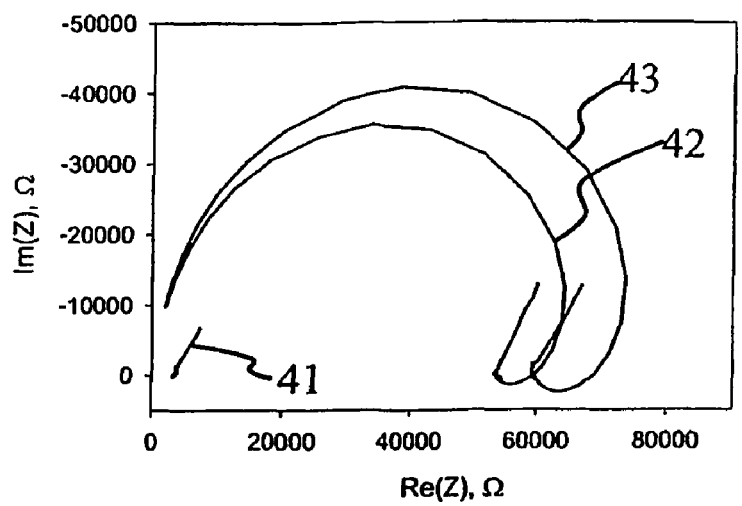
FIGS. 4A and 4B show graphical representations of electrical impedance spectra of sugar syrup with different sugar crystal contents.
Figure 4B:
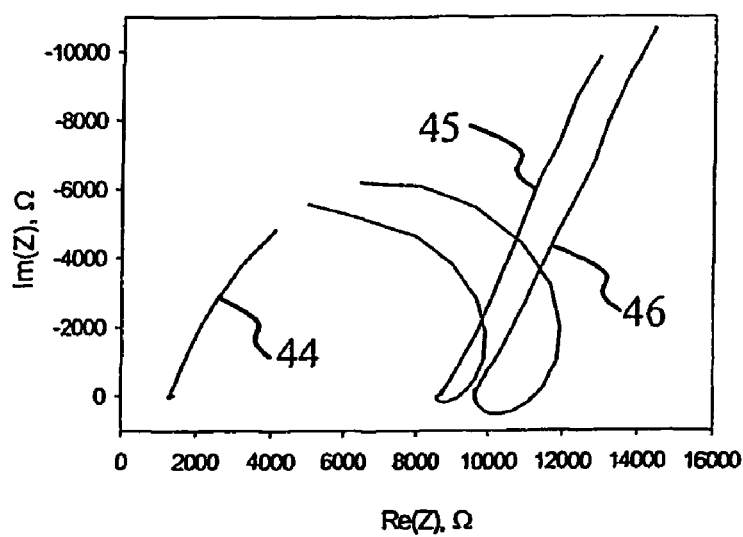

In FIGS. 4A and 4B EIS is produced for sugar syrup having different crystal contents. In the case with white sugar (see FIG. 4A), the EIS for the unsaturated syrup 41 (containing 20% by volume water and 80% saturated syrup) is significantly different from that for saturated syrup 42. By adding 10% by weight white sugar crystals into the saturated syrup, a spectrum 43 is produced. Electrical impedance spectra for unsaturated raw sugar syrup, saturated raw sugar syrup and saturated raw sugar syrup with 10% (by weight) raw sugar crystals are represented by 44, 45 and 46, respectively. By comparing the EIS for raw sugar in FIG. 4B with those for white sugar in FIG. 4A, it can be seen that the spectra for raw sugar syrup have a lower value of real impedance and different spectrum patterns from those for white sugar. This is due to the higher concentration of soluble impurity in raw sugar. As shown in FIGS. 4A and 4B, EIS can detect not only the crystal content of mother liquor but also the purity of mother liquor.

Figure 5A:
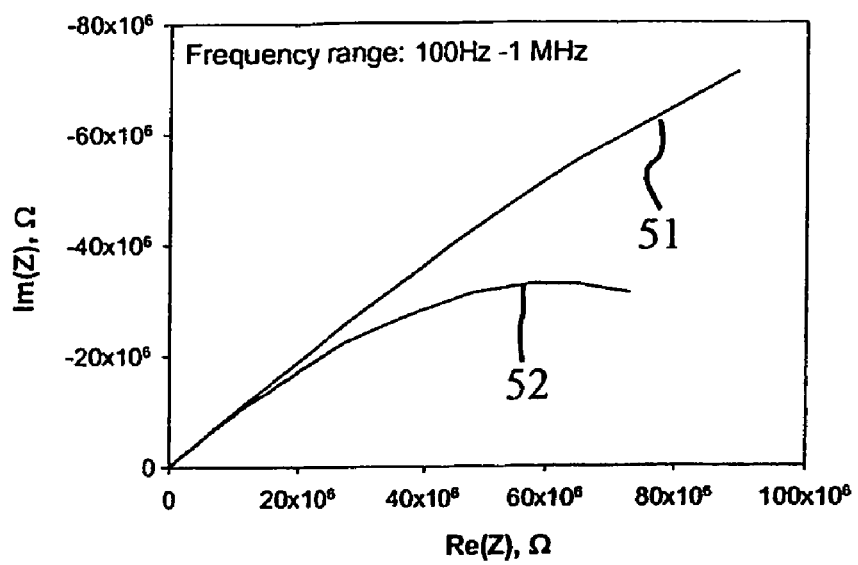
FIGS. 5A and 5B show graphical representations of electrical impedance spectra of water-oil emulsions.
Figure 5B:
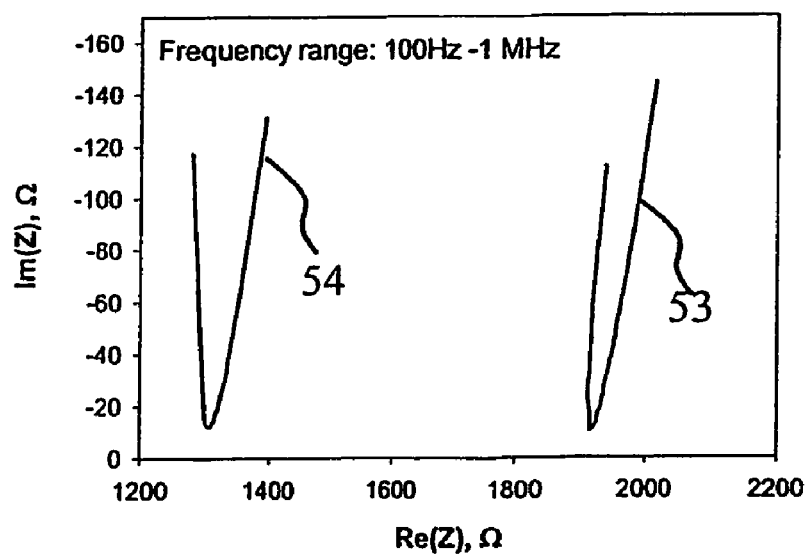

FIGS. 5A and 5B show examples of EIS curves for water-oil emulsions. Curve 51 shows the EIS for the water-in-oil emulsion with 25% (by volume) water whereas curve 52 shows the EIS for the emulsion with 50% water. FIG. 5B shows EIS for oil-in-water emulsions, and the spectra for 50% and 75% water are represented by 53 and 54, respectively. It can be seen that the EIS pattern for water-in-oil emulsions is different from that for oil-in-water emulsions. This difference will provide a basis for identifying emulsion type using EIS.

Figure 6:
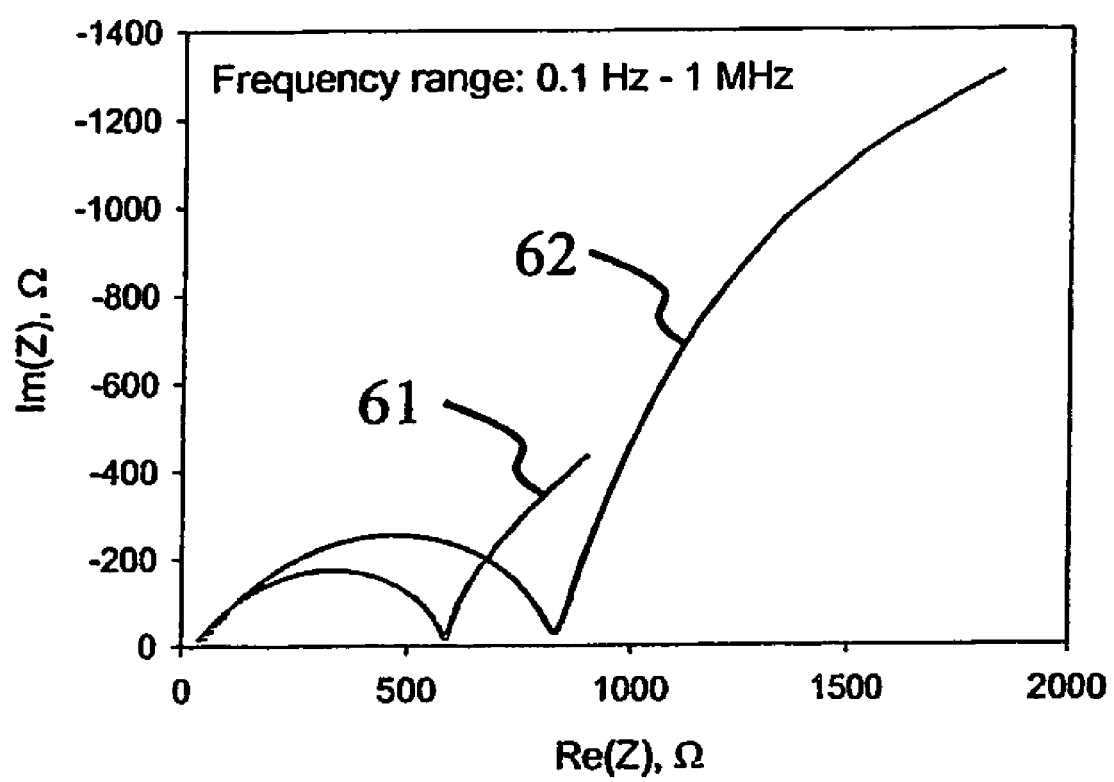
FIG. 6 shows graphical representations of electrical impedance spectra of liquid-solids slurries with different particle sizes.

FIG. 6 shows the EIS change of slurry with particle size under the same volumetric concentration of solids. It can be seen that for this particular particles the EIS for 30 μm particle size 61 is significantly changed to curve 62 when the particle size is reduced to 20 μm. It should be pointed out that EIS is not sensitive to particle size change when the size is higher than 50 μm. However, in situations where the particle size is smaller than 50 μm, it is possible to monitor the particle size by observing the change of EIS curve.

The froth phase in bubble flotation processes is a special type of multiphase fluid mixtures, in which the electrical and dielectric properties of components are different from each other. For example, the conductivity of water is several orders of magnitude higher than that for mineral particles. From the viewpoint of electrical behaviour of the froth phase, the inter-bubble lamellae containing water and solids can be regarded as a complex network of electrical conductance, inductance and capacitance. The structure of this network is sensitive to changes in the operating conditions of bubble flotation processes, and hence the effects of operating conditions, such as reagent dosages, feed flowrate and froth depth, on the flotation performance are reflected on the measured EIS. Therefore, the measurement of the electrical impedance of the froth phase over a wide range of excitation signal frequency would probe into the performance of flotation processes.

Figure 7:
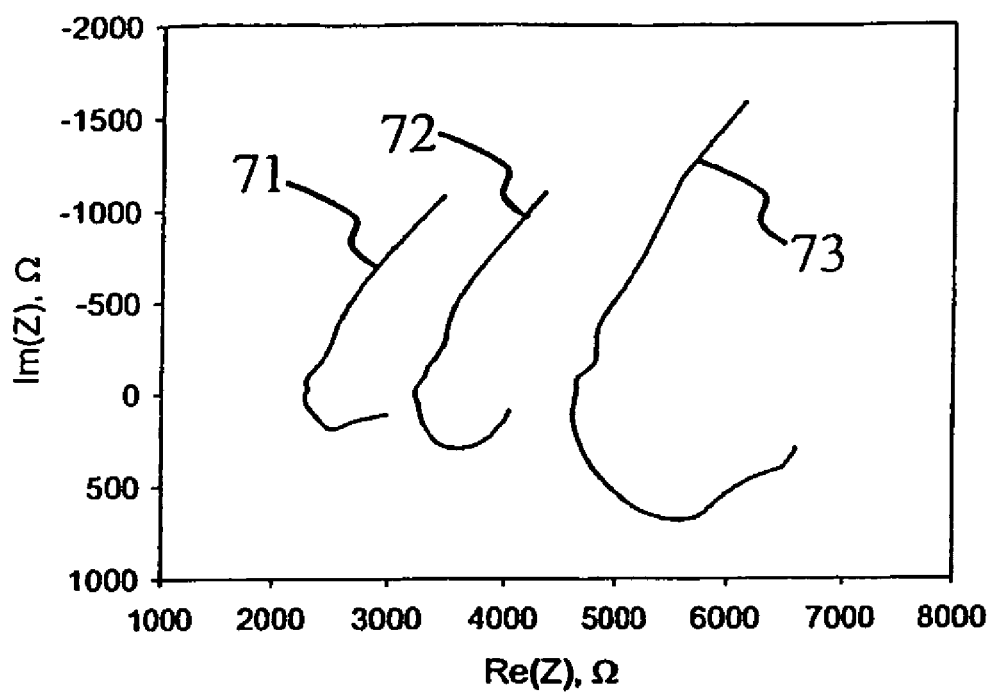
FIG. 7 shows graphical representations of electrical impedance spectra of froth (or foaming) phase with different characteristics.

FIG. 7 shows electrical impedance spectra measured in the froth phase of bubble flotation processes of one fine coal under various operating conditions. The spectra for 78%, 74% and 68% flotation yield are represented by 71, 72 and 73, respectively. It can be seen from the figure that the EIS spectra is closely correlated with the product yield. For this particular coal, the spectrum 71 is favourable in term of product yield. This favourable spectrum pattern can be conveniently used as the objective function for optimising operating conditions. In the bubble flotation of other materials, such as minerals, the pattern of EIS of the froth phase may be different from that shown in FIG. 7. However, the favourable pattern of EIS and associated operating conditions still can be identified using EIS as long as the flotation performance is sensitive to the changes in operating conditions.

Examples presented in FIGS. 3 to 7 clearly demonstrate that the electrical impedance spectrum can provide sufficient information regarding to the characteristics of multiphase fluid mixtures. In order to use these information for the on-line estimation of the characteristics of multiphase fluid mixtures, a mathematical or other type of relationship between the EIS and its corresponding characteristics of multiphase fluid mixtures is required. Among the various approaches for describing and modeling phenomena that are too complex for analytical methods or empirical rules, artificial intelligent data analysis techniques, particularly the artificial neural network (ANN) have shown great potential as an effective method for identifying or mapping complex non-linear relations without requiring specific knowledge of the model structure. Artificial neural network techniques are very efficient in computation due to the feedforward nature and also have higher tolerance to errors in the input data set than other parameter estimation approaches. Hence, a multiplayer perceptron artificial neural network (MLP-ANN) is a preferred but not an exclusive approach in the present invention to estimate characteristics of interest from the measured EIS of multiphase fluid mixtures. Other approaches, such as multivariate regression and ANN based on fuzzy logic are also useful in correlating the measured EIS with the characteristics of multiphase fluid mixtures.

Figure 8:
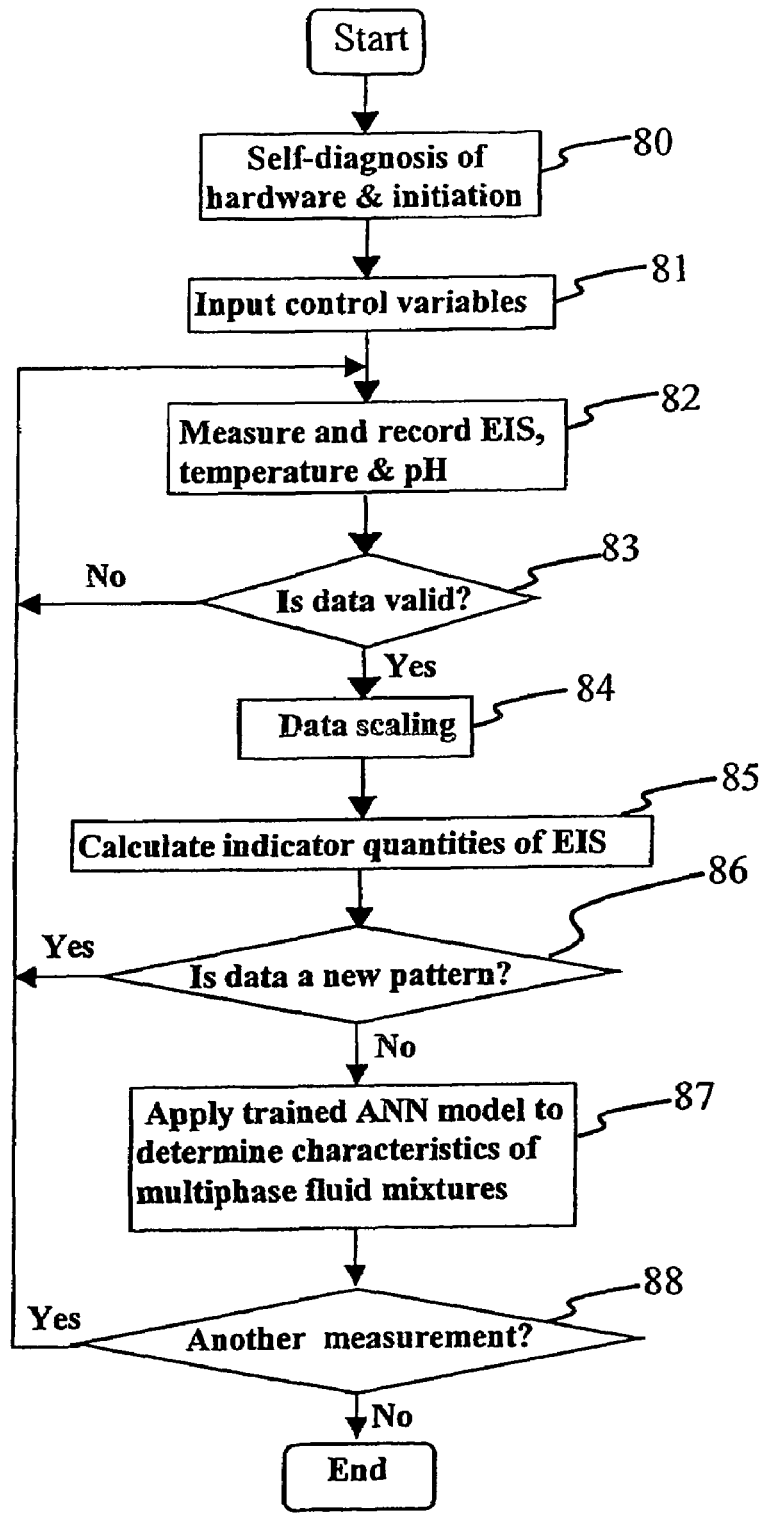
FIG. 8 shows a schematic diagram of a method for characterising multiphase fluid mixtures according to one embodiment of the present invention.

Based on observations derived from EIS measurements taken using the aforementioned apparatus it is possible to employ an automated procedure to identify characteristics of multiphase fluid mixtures. FIG. 8 is a flow chart showing a method for implementing this automated procedure.

As illustrated in FIG. 8, when the power is ON, the measurement unit 14 makes a diagnosis of itself and becomes initialised in step 80. Computing unit 15 then sends control variables to the measurement unit 14 in step 81. Control variables include the amplitude of AC signal generated by 14, frequency range, number of measurement points in the frequency range, and the like.

Once the measurement unit 14 receives control variables the electrical impedance spectrum, temperature and optionally pH are measured and recorded in step 82 using the aforementioned apparatus. It is preferred that the measurement of EIS, temperature and pH in step 82 are repeated several times in a short period of time and their average values are used for further processing. If the data is valid for a particular application as referenced by step 83 the computing unit is able to activate a data processor so as to scale the data into a suitable range of values as referenced by step 84. Alternatively if the data is not valid an alarm signal is provided to a display to notify an observer that the invalid data occurs and the measurement and recording step 82 is repeated.

After the data has been scaled into a suitable range the computing unit 15 is programmed to calculate the indicator quantities from the scaled EIS data as referenced by step 85. Then a software program performs a classification analysis of data pattern in step 86 to identify whether the EIS data pattern is unseen in the training stage of an artificial neural network (ANN) or in the development stage of a multivariate regression model. If the answer is yes an alarm signal is provided to a display to notify an observer that the new data pattern occurs and the measurement and recording step 82 is repeated. If the new data pattern repeatedly occurs, the computing unit 15 is programmed to retrain an ANN model or refit a multivariate regression model using a data set including the new data pattern. Alternatively if the data pattern is not a new one an output of at least one of the characteristics of the multiphase fluid mixtures is produced by the computing unit in the step 87. If there is no manual interruption then the measurement and recording step of item 82 is repeated.

In the data validation step, as referenced by item 83, data with a low precision, values close to pre-specified limits and significant noise are discarded to control the data quality for further processing. In ANN and multivariate analysis it is mandatory to scale the measured EIS and other data before the main business of analysis begins. This is because the measured EIS and other variables have different units and magnitude of values. Scaling methods useful in the present invention include column centring, standardisation and range scaling. Range scaling cause the values to fall between 0 to 1 or −1 to 1. These scaling methods are applied only to columns (i.e. data points at a same frequency from different measurements).

In order to capture all important frequency and signal amplitude dependent information, a number of frequency points are usually used in the measurement of EIS and the measurement is repeated with a few different amplitude of excitation signal. In applying mathematical approaches, such as artificial neural network and multivariate regression, to predict characteristics from measured EIS, the use of all data points in a spectrum will result in a very large dimension of input. An unnecessary large dimension of input variables will have adverse effects. For a fixed number of training data patterns, with the increase of input variables it becomes more sparse in the multi-dimensional space, and therefore degrades the learning performance. The generality of the trained ANN model may also be reduced due to inclusion of irrelevant or unimportant input variables. Apart from irrelevant and unimportant variables that cause large dimension of input variables, there may be correlation's between EIS data points measured at frequencies close to each other. Correlated inputs make the model more sensitive to the statistical peculiarities of the particular data sample, and they accentuate the overfitting problem and limit generalisation. Therefore, it is an important step in the present invention to calculate or extract from EIS indicator quantities with a much less number of variables but retaining sufficient information of the original spectrum.

The indicator quantities of the electrical impedance spectrum may include the real and imaginary impedance values at a number of selected frequencies, first and second derivatives of the spectrum at a number of selected frequencies, average values of imaginary impedance component over a selective range of real impedance, the parameters of a mathematical model for the representation of the impedance spectrum, and the latent variables or principal components, summarising the information contained in the original impedance spectrum, calculated from multivariate statistical methods, such as principal component analysis (PCA) and partial least-squares (PLS).

The method preferably includes calculating indicator quantities by fitting the electrical impedance spectrum to a mathematical model of the impedance spectrum. The mathematical model may further includes an electrical equivalent circuit model and empirical regression equations.

Figure 9:
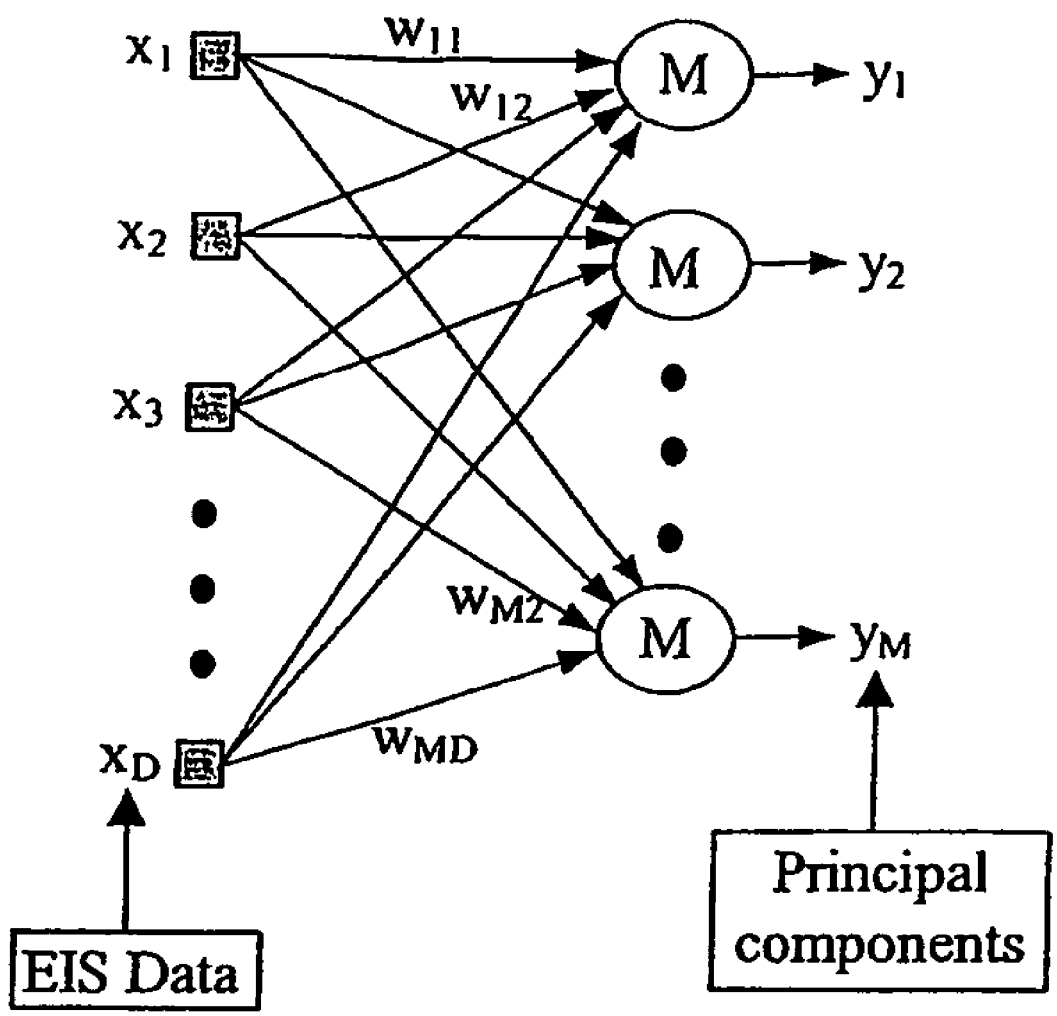
FIG. 9 shows a PCA neural network to project the data from D to M dimensions.

It is preferred that PCA implemented using an artificial neural network, as shown in FIG. 9, adapted with Hebbian learning or similar rules is used for calculating indicator quantities for the robustness. There are well-known algorithms that analytically computer PCA, but they have to solve matrix equations associated with singular value decomposition. When the matrices are ill-conditioned, the numerical solutions fail, while PCA neural networks provide more robust solutions.

If an indicator quantity data set has a pattern which has not been seen in the training stage of an ANN model or in the development stage of a multivariate regression model, the output of these model taking the data set as input will be erroneous. Therefore, it is necessary to check whether the pattern of a new data set is new. The classification of data patterns can be performed using ANN based approaches, such as unsupervised Bayesian clustering system, or the data reconstruction approach associated with PCA. If the indicator quantities calculated from a measured EIS (x) is represented by vector y, the reconstructed EIS is given by $$x' = W^T y,$$

where W is the weight matrix.

If the difference between the reconstructed EIS, x' and the measured EIS, x is larger than a specified threshold, the data pattern of the measured EIS can be considered as a new one. If this new pattern repeatedly occurs, it will become necessary to retrain an ANN model or refit a multivariate regression model.

In the prediction step, as referenced by item 87, the ANN model can be replaced by a multivariate regression model, a pattern matching algorithm or even a lookup table. When a lookup table is used in step 87, the comparison between indicator quantities of a measured EIS with reference indicator quantities will be used to determine characteristics of multiphase fluid mixtures.

The output from an trained ANN model or other types of relationship, such as lookup tables can be numerical values or qualitative indices, such as classification index.

The invention claimed is:

1. A method of analysing extraneous matter in a fluid including steps of receiving impedance data, the impedance data including real and imaginary impedance values measured across electrodes located in the fluid, recording an impedance spectrum at a plurality of time intervals at a predetermined amplitude of energy applied across the electrodes, calculating indicator quantities of the impedance spectrum for the received impedance spectrum data, comparing indicator quantities of the impedance spectrum with reference indicator quantities and determining at least one characteristic of at least one phase constituent in the multiphase fluid for the comparing steps.

2. The method as claimed in claim 1 wherein the indicator quantities include the minimum number of quantities required to model an original electrical impedance spectrum.

3. The method as claimed in claim 2 wherein the indicator quantities include one or more of the real and imaginary impedance values at a number of selected frequencies, first and second derivatives of the spectrum at a number of selected frequencies, average values of an imaginary impedance component over a selective range of real impedance, parameters of a mathematical model for a representation of the impedance spectrum and latent variables or principle components summarising information contained in an original impedance spectrum calculated from at least one multivariate statistical method.

4. The method as claimed in claim 3 wherein the multivariate statistical method includes a principle component analysis using an artificial neural network.

5. The method as claimed in claim 4 including checking whether a pattern of a new data set of indicator quantity data fits a predetermined pattern.

6. The method as claimed in claim 5 wherein the checking includes representing indicator quantities calculated from a measured electrical impedance spectrum EIS(x) by a vector y and calculating a reconstructed EIS given by $x'=W^T y$ where W is a weight matrix, whereby if for a difference between the reconstructed EIS, x' and the measured EIS, x is larger than a specified threshold, the data pattern of the measured EIS is recorded as a new one.

* * * * *